United States Patent [19]

Zavyalov et al.

[11] 3,960,884

[45] June 1, 1976

[54] METHOD OF PREPARING RACEMIC BIOTIN

[76] Inventors: Sergei Ivanovich Zavyalov, ulitsa Garibaldi, 23/56, korpus 4, kv. 54; Natalya Alexandrovna Rodionova, ulitsa Volochaevskaya, 17a, kv. 50; Zinaida Naumovna Parnes, Novo-Alexeevskaya ulitsa I, kv. 30; Galina Ilinichna Bolestova, Flotskaya ulitsa, 7, korpus 2, kv. 7, all of Moscow; Vladimir Vasilievich Filippov, ulitsa Mira, 40, kv. 41, Vladimir; Lidia Lvovna Zheleznaya, Leninsky prospekt, 60/2 kv. 5ii, Moscow, all of U.S.S.R.

[22] Filed: Apr. 24, 1974

[21] Appl. No.: 463,842

[52] U.S. Cl. ................... 260/309.7; 260/329 AM
[51] Int. Cl.² .......................................... C07D 49/34
[58] Field of Search ................................ 260/309.7

[56] References Cited
UNITED STATES PATENTS

| | | | |
|---|---|---|---|
| 2,460,225 | 1/1949 | Harris et al. | 260/309.7 X |
| 2,508,457 | 5/1950 | Harris | 260/309.7 X |
| 2,571,238 | 10/1951 | Harris et al. | 260/309.7 X |

*Primary Examiner*—Ethel G. Love
*Attorney, Agent, or Firm*—Haseltine, Lake & Waters

[57] ABSTRACT

A method of preparing racemic biotin comprises reacting 2,3,8,9-tetradehydrobiotin with triethylsilane and trifluoroacetic acid.

3 Claims, No Drawings

METHOD OF PREPARING RACEMIC BIOTIN

The present invention relates to a method of preparing racemic biotin which is a highly effective growth stimulant for microorganisms and is useful in the production of baker's yeast. Biotin (Vitamin H) may be also used as a medicine for treating hypertonia, atherosclerosis, dermopathy, and as a component of cosmetics and a bio-stimulant for cattle-breeding.

Known in the art is a method of preparing racemic biotin from cysteine and glutaric acid, which method comprises 16 stages. The desired product yield is 1.5 wt.%. (cf. S.A. Harris, D.E. Wolf, J. Am. Chem. Soc., 66, 1756 (1944).

This prior art method resides in that 4-benzoyl-amino-3-ketotetrahydrothiophane prepared from cysteine in 7 stages is subjected to crotonic condensation with γ-formylsuccinic acid methylate prepared from glutaric acid in 3 stages, followed by treating with hydroxylamine and reducing the resulting oxime to a mixture of two isomers (I) and (II) which differ from each other by the double bond position.

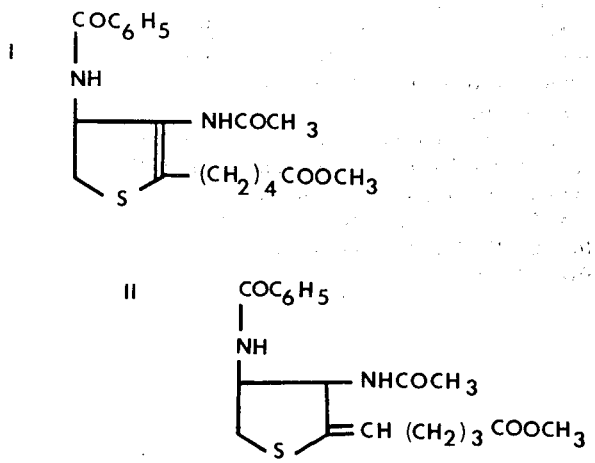

Catalytic hydrogenation of (I) results in a mixture of d,l-aminoesters, wherefrom dl-biotin and dl-allobiotin are then prepared in two stages.

Also known in the art is another method of preparing racemic biotin by catalytic hydrogenation of 2,3,8,9-tetradehydrobiotin (III) over molybdenum sulfide deposited onto alumina.

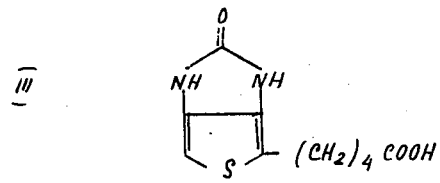

The former method has some disadvantages residing in that it comprises multi-stages and is comparatively complicated to be commercially implemented, since it involves handling metallic sodium in liquid ammonia and contemplates the use of phosgene.

The latter method has a disadvantage residing in a low and unstable yield of biotin, whereby this method cannot be implemented on a commercial scale.

In nature, biotin occurs in extremely small concentrations, wherefore there are no economically efficient methods of isolating biotin from naturally-occurring sources.

It is an object of the present invention to provide a method suitable for commercial implementation which would make it possible to increase the desired product yield.

This object is accomplished by a method of preparing racemic biotin, wherein, according to the present invention, 2,3,8,9-tetradehydrobiotin is reacted with triethylsilane and trifluoroacetic acid.

It is advisable to conduct the process at a temperature within the range of from 20° to 70°C.

2,3,8,9-tetradehydrobiotin, triethylsilane and trifluoroacetic acid should be preferably employed in a molar ratio of 1:2:9–10.

The method of the present invention is performed in the following manner.

A mixture comprising 2,3,8,9-tetradehydrobiotin, triethylsilane, and trifluoroacetic acid is maintained at a temperature ranging from 20° to 70°C for a period of from 20 to 150 hours. Then, the reaction mixture is evaporated to dryness. The residue is mixed with acetone and the precipitate is recrystallized from water. The desired product may also be isolated by another technique: after evaporating the reaction mixture to dryness, the residue is dissolved in alcohol, introduced into a column with silica gel and the desired product is eluted with acetone. The yield of purified racemic biotin is as high as 8 per cent.

The starting compound, viz. 2,3,8,9-tetradehydrobiotin may be prepared by a conventional method using thioacetate (IV) which is reacted with an aqueous alkali solution, followed by acidification:

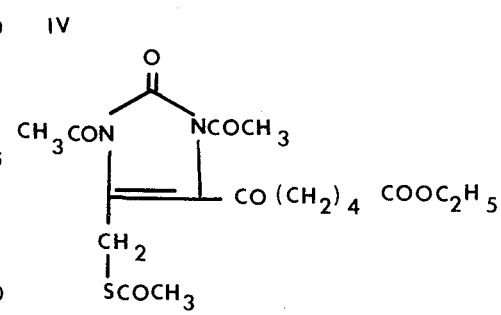

The term "thioacetate", as used herein, refers to the compound N,N-diacetyl-α-keto-α'-(acetylmercapto)-dehydrodesthiobiotin ethylate. Thioacetate, in turn, is prepared from commercially available ketodehydrodesthiobiotin ethylate (V), as described in [a] R. Duschinsky, L. A. Dolan, Jubilee Volume Barell, Basle, 1946, and in [b] Zavialov S. I., Rodionova N. A. USSR Inventor's Certificate, N386945 Bulletin of Inventions, N 27, Oct. 3, 1973. In this method, α-keto dehydrodesthiobiotin ethylate is heated with excess acetic anhydride and N, N-diacetyl-α-ketodehydrodesthiobiotin ethylate is isolated. The latter is brominated with N-bromosuccinimide in the presence of carbon tetrachloride to yield N, N-diacetyl-α-keto-α'-bromodehydrodesthiobiotin ethylate, which reacts with potassium thioacetate in acetone yielding N, N-diacetyl-α-keto-α'-(acetylmercapto)-dehydrodesthiobiotin.

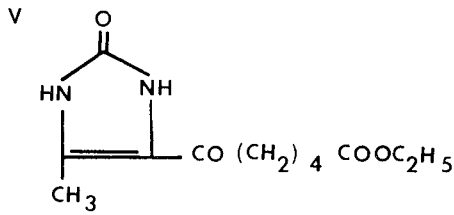

The method of the present invention makes it possible to increase the desired product yield and is commercially applicable.

For a better understanding of the present invention the following examples illustrating the preparation of racemic biotin are given hereinbelow.

EXAMPLE 1

A mixture of 0.432 g (0.0018 mol) of 2,3,8,9-tetradehydrobiotin, 0.42 g (0.0036 mol) of triethylsilane and 1.96 g (0.0172 mol) of trifluoroacetic acid is heated for 20 hours at 70°C, whereafter the solution is evaporated to dryness in vacuum; the residue is dissolved in a minimal amount of alcohol and the resulting solution is introduced into a column filled with silica gel; the products of ionic hydrogenation are eluted with acetone and thrice recrystallized from water to give 13 mg (3 wt.%) of racemic biotin melting at 213°–215°C with $R_f = 0.28$ (Support — silica gel G, solvent — ethyl acetate:alcohol in the ratio of 1:4, development with iodine vapors). IR-spectrum: 1,710; 1,690; 1,480; 1,320 $cm^{-1}$.

A mixed melt sample shows no depression with biotin prepared by the prior art method and has values of $R_f$ and IR-spectrum identical to those of biotin prepared by the prior art method.

EXAMPLE 2

A mixture of 0.5 g (0.0020 mol) of 2,3,8,9-tetradehydrobiotin, 0.486 g (0.0041 mol) of triethylsilane and 2.27 g (0.0199 mol) of trifluoroacetic acid is heated for 120 hours at 50°C, whereafter it is evaporated in vacuum and the residue is treated with 3 ml of acetone; the resulting precipitate is filtered off and 2–3 times recrystallized from water. The product yield is 0.038 g (8 wt.%); melting point 215°–217°C; $R_f = 0.28$ (support — silica gel G, solvent — alcohol: ethyl acetate =4:1, development with iodine vapours). A mixed sample shows no depression with biotin prepared by the prior art method. When tested on baker's yeast, the thus-obtained biotin shows a 43% activity of D-biotin.

What is claimed is:

1. A method of preparing racemic biotin, which comprises reacting 2,3,8,9-tetradehydrobiotin with triethylsilane and trifluoroacetic acid, followed by isolation off the racemic biotin.

2. A method as claimed in claim 1, wherein 2,3,8,9-tetradehydrobiotin, triethylsilane and trifluoroacetic acid are employed in a molar ratio of 1:2:9-10.

3. A method as claimed in claim 1, wherein the reaction is effected at a temperature within the range of from 20° to 70°C.

* * * * *